United States Patent
Tanaka

(10) Patent No.: US 9,433,205 B2
(45) Date of Patent: Sep. 6, 2016

(54) SUSPOEMULSION

(71) Applicant: SUMITOMO CHEMICAL COMPANY, LIMITED, Tokyo (JP)

(72) Inventor: Takuya Tanaka, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/381,484

(22) PCT Filed: Feb. 27, 2013

(86) PCT No.: PCT/JP2013/056053
§ 371 (c)(1),
(2) Date: Aug. 27, 2014

(87) PCT Pub. No.: WO2013/129690
PCT Pub. Date: Sep. 6, 2013

(65) Prior Publication Data
US 2015/0111860 A1     Apr. 23, 2015

(30) Foreign Application Priority Data

Feb. 29, 2012 (JP) ................................. 2012-043086

(51) Int. Cl.
| | | |
|---|---|---|
| A01N 25/04 | (2006.01) | |
| A01N 43/40 | (2006.01) | |
| A01N 51/00 | (2006.01) | |
| A01N 37/34 | (2006.01) | |
| A01N 43/54 | (2006.01) | |
| A01N 43/56 | (2006.01) | |
| A01N 43/78 | (2006.01) | |
| A01N 43/80 | (2006.01) | |
| A01N 47/40 | (2006.01) | |
| A01N 57/14 | (2006.01) | |

(52) U.S. Cl.
CPC .............. *A01N 25/04* (2013.01); *A01N 37/34* (2013.01); *A01N 43/40* (2013.01); *A01N 43/54* (2013.01); *A01N 43/56* (2013.01); *A01N 43/78* (2013.01); *A01N 43/80* (2013.01); *A01N 47/40* (2013.01); *A01N 51/00* (2013.01); *A01N 57/14* (2013.01)

(58) Field of Classification Search
CPC ............................ A01N 25/04; A01N 37/34
USPC ....................................................... 504/116
See application file for complete search history.

(56) References Cited

U.S. PATENT DOCUMENTS

2011/0257166 A1   10/2011  Damaceno et al.

FOREIGN PATENT DOCUMENTS

| CN | 102245025   | * 11/2011 | ........... C07D 111/11 |
|---|---|---|---|
| CN | 102245025 A |   11/2011 | |
| EP | 0 897 171 A1 |    2/1996 | |
| JP | 7-285803 A  |   10/1995 | |
| JP | 8-87803 A   |    3/1998 | |
| JP | 2000-344604 A | 12/2000 | |
| JP | 2002-293701 A | 10/2002 | |
| JP | 2003-321303 A | 11/2003 | |
| JP | 2007-126408 A |  6/2007 | |
| JP | 2011-16741 A  |  1/2011 | |
| WO | 99/40784 A1   |  8/1999 | |
| WO | WO 2011/030806 A1 | 3/2011 | |

OTHER PUBLICATIONS

International Search Report, mailed May 14, 2013, issued in PCT/JP2013/056053.
The First Office Action (including an English translation thereof) issued in the corresponding Chinese Patent Application No. 201380011086.1 on May 18, 2015.
European Patent Office Communication pursuant to Rules 70(2) and 70a(2) EPC issued in the corresponding European Patent Application No. 13754540.6 on Nov. 17, 2015.
European Patent Office Communication and extended search report issued in the corresponding European Patent Application No. 13754540.6 on Oct. 29, 2015.
Mu-Qian, "Chemicals of Wood and Forest Products-Prostaglandin", Encyclopedia of Chemical Technology, Pesticides, vol. 12, p. 462.
The Second Office Action (including an English translation thereof) issued in the corresponding Chinese Patent Application No. 201380011086.1 on Dec. 21, 2015.

* cited by examiner

*Primary Examiner* — Paul V Ward
(74) *Attorney, Agent, or Firm* — Birch, Stewart, Kolasch & Birch, LLP

(57) ABSTRACT

The present invention relates to a suspoemulsion comprising the following ingredients (1), (2), (3), (4), (5), and (6):
an ingredient (1): low water-soluble liquid pesticidal ingredient,
an ingredient (2): low water-soluble pesticidal active ingredient which is solid at normal temperature,
an ingredient (3): polyoxyalkylene block copolymer,
an ingredient (4): phosphate ester salt and/or sulfate ester salt of polyoxyethylene aryl phenyl ether,
an ingredient (5): ligninsulfonic acid salt, and
an ingredient (6): water.

The suspoemulsion of the present invention is a formulation having excellent storage stability, which suppresses the particle growth of dispersoids of an ingredient (1) and an ingredient (2) during storage at high temperature and low temperature, and causes neither aggregation nor separation of dispersoids, nor formation of a hard cake, nor a change in appearance.

15 Claims, No Drawings

SUSPOEMULSION

TECHNICAL FIELD

The present invention relates to a novel suspoemulsion containing a pesticidal active ingredient.

BACKGROUND ART

There has hitherto been known, as a pesticidal formulation containing two kind of pesticidal active ingredients, a suspoemulsion in which a liquid pesticidal ingredient is emulsified and also a solid pesticidal ingredient is suspended in water.

CITATION LIST

Patent Literature

[Patent Literature 1]
  JP 8-67603 A

SUMMARY OF INVENTION

Technical Problem to be Dissolved by the Invention

A suspoemulsion is a formulation in which oil droplets of a liquid pesticidal ingredient and particles of a solid pesticidal ingredient are dispersed together in water, and there is a need that these ingredients are stably dispersed together in water not only immediately after production, but also after storage. However, when a conventional suspoemulsion is stored under severe environment at high temperature or low temperature, oil droplets and particles (dispersoids) dispersed in water may sometimes cause a change such as particle growth, separation of an aqueous layer and formation of a hard cake due to aggregation and precipitation of dispersoids, or a change in appearance such as creaming of the formulation, and thus the conventional suspoemulsion was not necessarily sufficient in storage stability.

Solution to Problem

The present inventors have studied in view of these circumstances and found that a suspoemulsion containing a polyoxyalkylene block copolymer, a phosphate ester salt and/or a sulfate ester salt of polyoxyethylene aryl phenyl ether, and a ligninsulfonic acid salt is a formulation having excellent storage stability, which suppresses the particle growth of dispersoids, namely, oil droplets of a liquid pesticidal ingredient and particles of a solid pesticidal ingredient, and also cause neither aggregation nor separation of dispersoids, nor formation of a hard cake, nor a change in appearance, during storage at high temperature and low temperature. Thus, the present invention has been completed. Namely, the present invention will be shown.

[1] A suspoemulsion comprising the following ingredients (1), (2), (3), (4), (5), and (6):
  an ingredient (1): low water-soluble liquid pesticidal ingredient,
  an ingredient (2): low water-soluble pesticidal active ingredient which is solid at normal temperature,
  an ingredient (3): polyoxyalkylene block copolymer,
  an ingredient (4): phosphate ester salt and/or sulfate ester salt of polyoxyethylene aryl phenyl ether,
  an ingredient (5): ligninsulfonic acid salt, and
  an ingredient (6): water.

[2] The suspoemulsion according to the above item [1], wherein the respective amounts of the ingredients (1), (2), (3), (4), (5), and (6) are 0.1 to 49.5 w/v %, 0.1 to 49.5 w/v %, 0.1 to 10 w/v %, 0.1 to 10 w/v %, 0.1 to 10 w/v %, and 50 to 99.5 w/v %, based on the total amount.

[3] The suspoemulsion according to the above item [1] or [2], wherein the ingredient (1) is a low water-soluble pesticidal active ingredient which is liquid at normal temperature.

[4] The suspoemulsion according to the above item [1] or [2], wherein the ingredient (1) is in a state that a low water-soluble pesticidal active ingredient is dissolved in a hydrophobic liquid.

[5] The suspoemulsion according to the above item [3] or [4], wherein the low water-soluble pesticidal active ingredient is an insecticidal active ingredient.

[6] The suspoemulsion according to the above item [3] or [4], wherein the low water-soluble pesticidal active ingredient is a pyrethroid compound.

[7] The suspoemulsion according to the above item [3] or [4], wherein the low water-soluble pesticidal active ingredient is esfenvalerate.

[8] The suspoemulsion according to any one of the above items [1] to [7], wherein the ingredient (2) is an insecticidal active ingredient.

[9] The suspoemulsion according to any one of the above items [1] to [7], wherein the ingredient (2) is a neonicotinoid compound.

[10] The suspoemulsion according to any one of the above items [1] to [7], wherein the ingredient (2) is clothianidin.

Unless otherwise specified, "normal temperature" as used in the specification means 5 to 35° C., "low water-soluble" means that the solubility in 100 mL of water at 25° C. is 1 g or less, and "w/v %" means "weight/volume %".

Effects of Invention

According to the present invention, it is possible to provide an excellent suspoemulsion which suppresses the particle growth of dispersoids (namely, an emulsified low water-soluble liquid pesticidal ingredient, and a suspended low water-soluble pesticidal active ingredient which is solid at normal temperature), and also cause neither aggregation nor separation of dispersoids, nor formation of a hard cake, nor a change in appearance, and is physicochemically stable over a long period of time, thus causing no deterioration of bioefficacy, during storage at high temperature and low temperature.

DESCRIPTION OF EMBODIMENTS

The suspoemulsion of the present invention contains an ingredient (1), namely, a low water-soluble liquid pesticidal ingredient.

First, the ingredient (1) includes a low water-soluble pesticidal active ingredient which is liquid at normal temperature. Among the low water-soluble pesticidal active ingredient, preferred is a compound having pesticidal activity, which has solubility in 100 mL at 25° C. of 0.1 g or less.

Examples of the ingredient (1) include those in which a low water-soluble pesticidal active ingredient is dissolved in a hydrophobic liquid, namely, those obtained by dissolving a low water-soluble pesticidal active ingredient in a hydrophobic liquid. The low water-soluble pesticidal active ingredient may be either solid or liquid at normal temperature as long as it is dissolved in a hydrophobic liquid. As used herein, the low water-soluble pesticidal active ingredient which is solid at normal temperature is a compound having pesticidal activity, which usually has a melting point of 35° C. or higher, and preferably lower than 80° C., and also has a solubility in 100 mL of water at 25° C. of 1 g or less, and preferably 0.1 g or less.

Examples of the low water-soluble pesticidal active ingredient used in the ingredient (1) include an insecticidal active ingredient, a fungicidal active ingredient, an herbicidal active ingredient, an insect growth regulating active ingredient and a plant growth regulating active ingredient.

Examples of the insecticidal active ingredient include pyrethroid compounds such as pyrethrin, allethrin, permethrin, cypermethrin, cyhalothrin, cyfluthrin, tralomethrin, fenpropathrin, bifenthrin, fenvalerate (also including esfenvalerate), flucythrinate, fluvalinate, acrinathrin, cycloprothrin, ethofenprox, silafluofen, tefluthrine, and deltamethrin; organophosphorus compounds such as cyanophos, fenthion, fenitrothion, dichlofenthion, pirimiphos-methyl, diazinon, isoxathion, chlorpyrifosmethyl, chlorpyrifos, phenthoate, ethylthiometon, phosalone, methidathion, prothiofos, profenofos, and EPN; carbamate compounds such as isoprocarb, fenocarb, carbosulfan, benfuracarb, and alanycarb; and pyridalyl.

Examples of the fungicidal active ingredient include organophosphorus compounds such as iprobenfos, edifenphos, and tolclofos-methy; melanin biosynthesis inhibiting compounds such as fenoxanil; acid amide compounds such as metalaxyl M and cyflufenamid; sterol biosynthesis inhibiting compounds such as triflumizole, prochloraz, pefurazoate, myclobutanil, propiconazole, and tetraconazole; strobilurin compounds such as trifloxystrobin and pyraclostrobin; anilinopyrimidine compounds such as cyprodinil; isoprothiolane, and diflumetorim.

Examples of the herbicidal active ingredient include phenoxy acid compounds such as MCPB, cyhalofop-butyl, fluazifop, and fluazifop P; carbamate compounds such as chlorpropham, benthiocarb, esprocarb, and molinate; acid amide compounds such as alachlor, pretilachlor, metolachlor, butachlor, dimethenamid, and napropamide; triazine compounds such as dimethametryn; dinitroaniline compounds such as trifluralin, bethrodine, and pendimethalin; aromatic carboxylic acid compounds such as dithiopyr; nitrile compounds such as ioxynil; cyclohexanedion compounds such as sethoxydim and clethodim; butamifos, indanofan, benfuresate, and carfentrazone-ethyl.

Examples of the insect growth regulating active ingredient include pyriproxyfen.

Examples of the plant growth regulating active ingredient include trinexapac-ethyl.

These low water-soluble pesticidal active ingredients can be used alone or as a mixture of two or more thereof.

Examples of the hydrophobic liquid include aromatic hydrocarbon, aliphatic hydrocarbon, alcohols, ketones, eaters, ethers, mineral oil, and vegetable oil. Examples of the aromatic hydrocarbon include toluene, xylene, alkylbenzene, phenylxylylethane, and a mixture thereof. Commercially available solvents can be used as they are as the aromatic hydrocarbon, and examples of the commercially available solvent include Hisol SAS-296 (mixture of 1-phenyl-1-xylylethane and 1-phenyl-1-ethylphenylethane, manufactured by Nippon Oil Co., Ltd.), Solvesso 100 (aromatic hydrocarbons, manufactured by ExxonMobil Chemical Company), Solvesso 150 (aromatic hydrocarbon, manufactured by ExxonMobil Chemical Company), Solvesso 150ND (aromatic hydrocarbons, manufactured by ExxonMobil Chemical Company), Solvesso 200 (aromatic hydrocarbons, manufactured by ExxonMobil Chemical Company), and Solvesso 200ND (aromatic hydrocarbons, manufactured by ExxonMobil Chemical company). Examples of the aliphatic hydrocarbon include paraffin and olefin, and commercially available solvents can be used as they are as the aliphatic hydrocarbon. Examples of the commercially available solvent include Isoper L (isoparaffins, manufactured by ExxonMobil Chemical Company), Isoper M (isoparaffins, manufactured by ExxonMobil Chemical Company), Exxsol D80 (mixed solvent of paraffins and cycloparaffins, manufactured by ExxonMobil Chemical Company), Exxsol D110 (mixed solvent of paraffins and cycloparaffins, manufactured by ExxonMobil Chemical Company), Exxsol D130 (mixed solvent of paraffins and cycloparaffins, manufactured by ExxonMobil Chemical Company), MORESCO WHITE P-40 (liquid paraffins, manufactured by MORESCO Corporation), MORESCO WHITE P-70 (liquid paraffins, manufactured by MORESCO Corporation), Linealene 12 (α-olefins, manufactured by Idemitsu Kosan Co., Ltd.), and Linealene 14 (α-olefin, manufactured by Idemitsu Kosan Co., Ltd.). Examples of the esters include fatty acid ester, and commercially available solvents can be used as they are as the ester, and examples of the commercially available solvent include RIC-CIZER C-101 (castor oil fatty acid ester, manufactured by Itoh Oil Chemicals Co., Ltd.), RIC-CIZER C-88 (vegetable oil-based fatty acid ester, manufactured by ITOH OIL CHEMICALS CO., LTD.), RIC-CIZER C-401 (castor oil fatty acid ester, manufactured by ITOH OIL CHEMICALS CO., LTD.), RIC-CIZER S-8 (castor oil-based dibasic acid ester, manufactured by ITOH OIL CHEMICALS CO., LTD.), Stepan C-25 (mixture of methyl caprylate and methyl caprate, manufactured by Stepan Company), Stepan C-42 (mixture of methyl myristate and methyl laurate, manufactured by Stepan Company), Stepan C-65 (mixture of methyl palmitate and methyl oleate, manufactured by Stepan Company), Steposol ME (mixture of methyl oleate and methyl linoleate, manufactured by Stepan Company), and Steposol ROE-W (canola oil methyl ester, manufactured by Stepan Company). Examples of the vegetable oil include soybean oil, olive oil, linseed oil, cotton seed oil, rapeseed oil, and castor oil. It is possible to select, as the hydrophobic liquid, those which do not dissolve or slightly dissolve the below-mentioned ingredient (2).

When the suspoemulsion of the present invention contains the hydrophobic liquid, the suspoemulsion of the present invention usually contains the hydrophobic liquid in the amount of 0.01 to 44.5 w/v %, and preferably 0.2 to 39.5 w/v %.

The suspoemulsion of the present invention usually contains the ingredient (1) in the amount of 0.1 to 49.5 w/v %, and preferably 1 to 49.5 w/v %.

When the ingredient (1) is the one that the low water-soluble pesticidal active ingredient is dissolved in the hydrophobic liquid, the ingredient (1) usually contains the low water-soluble pesticidal active ingredient and the hydrophobic liquid in a weight ratio within a range of 10:90 to 90:10, and preferably 20:80 to 80:20.

The suspoemulsion of the present invention contains the ingredient (2), namely, a low water-soluble pesticidal active ingredient which is solid at normal temperature. The ingredient (2) is a low water-soluble pesticidal active ingredient which is solid at normal temperature, and the melting point is usually 35° C. or higher, and preferably 80° C. or higher, and the solubility in 100 mL of water at 25° C. is 1 g or less, and preferably 0.1 g or less. Furthermore, an ingredient which does not dissolve, or slightly dissolves in the ingredient (1) is preferred as the ingredient (2). It is possible to select, as the ingredient (2), a compound having pesticidal activity in which the solubility in 100 g of the component (1) at 25° C. is usually 10 g or less, preferably 1 g or less, more preferably 0.1 g or less, and most preferably 0.01 g or less. The solubility can be determined in the following manner. That is, an ingredient (2) is added to an ingredient (1), followed by mixing with stirring. After being left to stand in a constant temperature water bath at 25° C., the supernatant containing the ingredient (2) in a saturated state is isolated and filtered to obtain a solution, and then a prescribed amount of an internal standard fluid is added to prepare a sample liquid for analysis. Using the sample liquid for analysis, high-performance liquid chromatography is performed, thus enabling the measurement of the solubility.

Examples of the low water-soluble pesticidal active ingredient which is solid at normal temperature to be used in the ingredient (2) include an insecticidal active ingredient, a fungicidal active ingredient, an herbicidal active ingredient, an insect growth regulating active ingredient, and a plant growth regulating active ingredient.

Examples of the insecticidal active ingredient include neonicotinoid compounds such as imidacloprid, acetamiprid, thiacloprid, thiametoxam, and clothianidin; nereistoxin compounds such as bensultap; carbamate compounds such as carbaryl and thiodicarb; diamide compounds such as flubendiamide and chlorantraniliprole: phenylpyrazole compounds such as fipronil and ethiprole; macrolide compounds such as emamectin benzoate, milbemectin, lepimectin, and spinosad, pymetrozine, flonicamid, chlorfenapyr, diafenthiuron, indoxacarb MP, metaflumizone, metaldehyde, and tolfenpyrad.

Examples of the fungicidal active ingredient include organosulfur compounds such as ziram, maneb, manzeb, polycarbamate, propineb, thiuram, and thiadiazine; melanin biosynthesis inhibiting compounds such as fthalide, triclazole, pyroquilon, carpropamide, and diclocymet; benzimidazole compounds such as thiophanate-methyl, benomyl, and diethofencarb; dicarboxyimide compounds such as iprodione and procymidone; acid amide compounds such as mepronil, flutolanil, boscalid, fluopicolide, furametpyr, thifluzamide, penthiopyrad, metalaxyl, fenhexamid, mandipropamid, tiadinil, and isotianil, sterol biosynthesis inhibiting compounds such as oxpoconazole fumarate, triadimefon, bitertanol, fenbuconazole, hexaconazole, tebuconazole, difenoconazole, ipconazole, imibenconazole, cyproconazole, simeconazole, metconazole, fenarimol, and triforine; strobilurin compounds such as azoxystrobin, kresoximmethyl, metominostrobin, orysastrobin, famoxadone, and fenamidone; anilinopyrimidine compounds such as mepanipyrim; thiazolecarboxamide compounds such as ethaboxam; probenazole, ferimzone, diclomezine, pencycuron, fluoroimide, captan, chlorothalonil, dithianon, quinoxaline series, fludioxonil, oxolinic acid, fluazinam, cymoxanil, iminoctadine albesilate, dimethoroph, benthiavalicarb-isopropyl, cyazofamid, and amisulbrom.

Examples of the herbicidal active ingredient include phenoxy acid compounds such as MCPA, MCPP, mecoprop P, triclopyr, clomeprop, and quizalofop-ethyl; carbamate compounds such as phenmedipham, desmedipham, and pyributicarb; acid amide compounds such as thenylchlor, bromobutide, etobenzanide, diflufenican, mefenacet, cafenstrole, propyzamide, isoxaben, and flupoxam; urea compounds such as diuron, linuron, siduron, dimuron, cumyluron, karbutilate, isouron, and tebuthiuron; sulfonylurea compounds such as bensulfuron-methyl, ethoxysulfuron, pyrazosulfuron-ethyl, azimsulfuron, halosulfuronmethyl, flazasulfuron, nicosulfuron, rimsulfuron, thifensulfuron-methyl, imazosulfuron, cyclosulfamuron, chlorimuron-ethyl, flucetosulfuron, metsulfuron-methyl, and iodosulfuron-methyl-sodium; pyrimidyloxybenzoic acid compounds such as pyriminobac-methyl, penoxsulam, and florasulam, triazine compounds such as simazine, atrazine, cyanazine, simetryn, prometryn, metribuzin, triaziflam, and metamitron; dieazine compounds such as terbacil, bromacil, lenacil, chloridazon, and bentazone; diazole compounds such as pyrazolate, pyrazoxyfen, benzofenap, pyraclonil, pyraflufen-ethyl, oxadiazon, and oxadiargyl; dinitroaniline compounds such as prodiamine and oryzalin; aromatic carboxylic acid compounds such as dicamba, imazaquin, and imazamox-ammonium; nitrile compounds such as dichlobenil and chlorthiamid; cyclohexanedion compounds such as tepraloxydim; phenylphthalimide compounds such as chlorphthalim and flumioxazin; triketone compounds such as tefuryltrione and mesotrione, quinoclamin, pentoxazone, oxaziclomefone, benzobicyclon, fluthiacet-methyl, fentrazamide, and pyriftalid.

Examples of the insect growth regulating active ingredient include diflubenzuron, teflubenzuron, lufenuron, flufenoxoron, chlorfluazuron, novaluron, tebufenozide, chromafenozide, methoxyfenozide, buprofezin, and cyromazine.

Examples of the plant growth regulating active ingredient include auxin compounds such as indolebutyric acid, 1-naphthylacetamide, ethychlozate, dichlorprop, and 4-CPA; cytokinin compounds such as benzylaminopurine and forchlorfenuron; gibberellin, maleic hydrazide potassium, uniconazole P, paclobutrazol, flurprimidol, prohexadione-calcium, and calcium peroxide.

These low water-soluble pesticidal active ingredients which are solid at normal temperature can be used alone or as a mixture of two or more thereof.

The suspoemulsion of the present invention usually contains the ingredient (2) in the amount of 0.1 to 49.5 w/v %, and preferably 1 to 49.5 w/v %.

The suspoemulsion of the present invention contains the ingredient (3), namely, a polyoxyalkylene block copolymer.

Examples of the ingredient (3) include a polyoxyethylene-polyoxypropylene block copolymer.

The ingredient (3) usually has a HLB value of 5 to 20, preferably 8 to 19, and more preferably 11 to 18.

Commercially available agents can be used as the ingredient (3), and examples thereof include STEP-FLOW 26 (manufactured by Stepan Company, HLB 13), and TOXIMUL 8323 (manufactured by Stepan Company, HLB 17).

The suspoemulsion of the present invention usually contains the ingredient (3) in the amount of 0.1 to 10 w/v %, and preferably 0.5 to 5 w/v %.

The suspoemulsion of the present invention contains the ingredient (4), namely, a phosphate ester salt of polyoxyethylene aryl phenyl ether and/or a sulfate ester salt of polyoxyethylene aryl phenyl ether.

The ingredient (4) is a phosphoric acid ester type or sulfuric acid ester type anionic surfactant. Examples of the ingredient (4) include a phosphate ester salt of polyoxyethylene tristyryl phenyl ether and a sulfate ester salt of polyoxyethylene tristyryl phenyl ether.

Examples of the salt of the ingredient (4) include a potassium salt, a sodium salt, an ammonium salt, and various amine salts.

The average addition molar number of an oxyethylene (EO) group of polyoxyethylene chain of the ingredient (4) is usually 6 to 20, and preferably 7 to 16.

Commercially available agents can be used as the ingredient (4), and examples thereof include Soprophor FLK (manufactured by Rhodia, Inc., phosphoric acid potassium salt in which the average addition molar number of an EO group is 16), Soprophor FL (manufactured by Rhodia, Inc., phosphoric acid amine salt in which the average addition molar number of an EO group is 16), Soprophor 4D384 (manufactured by Rhodia, Inc., and ammonium sulfate in which the average addition molar number of an EO group is 16).

The suspoemulsion of the present invention usually contains the ingredient (4) in the amount of 0.1 to 10 w/v %, and preferably 0.5 to 5 w/v %.

The suspoemulsion of the present invention contains the ingredient (5), namely, a ligninsulfonic acid salt.

Examples of the salt of the ingredient (5) include a sodium salt, a potassium salt, and an ammonium salt.

The sulfonation degree of the ingredient (5) is usually 0.1 to 5.0, preferably 0.5 to 4.0, and more preferably 1.5 to 2.5.

Commercially available agents can be used as the ingredient (5), and examples thereof include REAX 910 (manufactured by MeadWestvaco Corporation, sodium salt having a sulfonation degree of 1.7), REAX 81A (manufactured by MeadWestvaco Corporation, sodium salt having a sulfonation degree of 1.9), REAX 82 (manufactured by MeadWestvaco Corporation, sodium salt having a sulfonation degree of 2.0), and REAX 83A (manufactured by MeadWestvaco Corporation, sodium salt having a sulfonation degree of 2.1).

The suspoemulsion of the present invention usually contains the ingredient (5) in the amount of 0.1 to 10 w/v %, and preferably 0.5 to 5 w/v %.

The suspoemulsion of the present invention contains the ingredient (6), namely, water. Examples of water include hard water containing calcium ions and magnesium ions, or deionized water in which dissolved ions have been removed by an ion-exchange resin.

The suspoemulsion of the present invention usually contains the ingredient (6) in the amount of 50 to 99.5 w/v %, and preferably 50 to 90 w/v %.

In the suspoemulsion of the present invention, a ratio of the weight of the ingredient (1) to the sum of the weight of ingredient (3) and the weight of the ingredient (4) (namely, weight of ingredient (1):(weight of ingredient (3)+weight of ingredient (4))) is usually 1:2 to 1:0.01, and preferably 1:1 to 1:0.05. In the suspoemulsion of the present invention, a ratio of the sum of the weight of the ingredient (2) to the sum of the weight of the ingredient (4) and the weight of the ingredient (5) (namely, weight of ingredient (2): (weight of ingredient (4)+weight of ingredient (5)) is usually 1:2 to 1:0.01, and preferably 1:1 to 1:0.05.

If necessary, the suspoemulsion of the present invention further contains a dispersing agent, a defoamer, a thickener, a preservative agent, and an antifreezing agent.

Examples of the dispersing agent include natural polysaccharides such as gum arabic; natural water-soluble polymers such as gelatin and collagen; water-soluble semisynthetic polysaccharides such as carboxymethyl cellulose, methyl cellulose, and hydroxypropyl cellulose; and water-soluble synthetic polymers such as polyvinyl alcohol and polyvinyl pyrrolidone.

When the suspoemulsion of the present invention contains a dispersing agent, the content of the dispersing agent in the suspoemulsion of the present invention is usually within a range of 0.5 to 10 w/v %.

Specific examples of the defoamer include silicone-based defoamers such as Antifoam C (manufactured by Dow Corning Corporation), Antifoam C Emulsion (manufactured by Dow Corning Corporation), Rhodorsil 454 (manufactured by Rhodia, Inc.), Rhodorsil Antifoam 432 (manufactured by Rhodia, Inc.), TSA730 (manufactured by Toshiba Silicone Co., Ltd.), TSA731 (manufactured by Toshiba Silicone Co., Ltd.), TSA732 (manufactured by Toshiba Silicone Co., Ltd.), YMA6509 (manufactured by Toshiba Silicone Co., Ltd.); and fluorine-based defoamers such as Fluowet PL80 (manufactured by Clariant Corporation).

The content of the defoamer in the suspoemulsion of the present invention is usually within a range of 0 to 5 w/v %.

Examples of the thickener include natural polysaccharides such as xanthan gum, rhamsan gum, locust bean gum, carrageenan, and welan gum, synthetic polymers such as sodium polyacrylate; semisynthetic polysaccharides such as carboxymethyl cellulose; mineral fine powders such as magnesium aluminum silicate, smectite, bentonite, hectorite, and fumed silica; and alumina sol.

The content of the thickener in the suspoemulsion of the present invention is usually within a range of 0 to 10 w/v %.

The viscosity of the suspoemulsion of the present invention is preferably within a range of 500 to 3,500 mPa·s (B type viscometer, Spindle No. 2, 6 rpm) at 20° C. The viscosity can be measured, for example, using an RB80 type viscometer (TOKI SANGYO CO., LTD.).

Examples of the preservative agent include a p-hydroxybenzoic acid ester, a salicylic acid derivative, and an isothiazolin-3-one derivative.

The content of the preservative agent in the suspoemulsion of the present invention is usually within a range of 0 to 5 w/v %.

Examples of the antifreezing agent include water-miscible monoalcohols such as propanol; and water-miscible diols such as ethylene glycol and propylene glycol.

The content of the antifreezing agent in the suspoemulsion of the present invention is usually within a range of 0 to 10 w/v %.

The suspoemulsion of the present invention is a formulation in which an ingredient (1) is emulsified in an aqueous continuous phase including an ingredient (3), ingredient (4), an ingredient (5), and an ingredient (6), and in which an ingredient (2) is suspended. In the aqueous continuous phase, an ingredient (3), an ingredient (4), and an ingredient (5) are dissolved in an ingredient (6). The ingredient (3) is sometimes dissolved in the ingredient (1).

In the suspoemulsion of the present invention, the particle diameter (volume median diameter) of the ingredient (1) is usually within a range of 20 μm or less, and preferably 0.1 to 10 μm. The particle diameter (volume median diameter) of the ingredient (2) is usually within a range of 20 μm or less, and preferably 0.1 to 10 μm. The volume median diameter is the value calculated by analyzing images of a lot of particles measured by a laser diffraction scattering method based on Mie scattering theory. The volume median diameter means the value the total volume of particles having a value smaller than the value and the value the total volume of particles having a value larger than the value respectively account for 50% of the total volume of all particles. Examples of the measuring machine of the volume median diameter include Mastersizer 2000 [manufactured by Sysmex Corporation].

The suspoemulsion of the present invention can be produced, for example, by the following method.

Method 1: An ingredient (3), an ingredient (4), and an ingredient (5) are dissolved in an ingredient (6), and then an ingredient (1) and an ingredient (2) and, if necessary, auxiliaries such as a dispersing agent and a defoamer are added. After mixing, the mixture is simultaneously subjected to pulverization/suspension and emulsification by a wet milling technique using media such as glass beads and zirconia beads and, if necessary, auxiliaries such as a defoamer, a thickener, a preservative agent, and an antifreezing agent are added.

Method 2: An ingredient (3) and/or an ingredient (4), and/or an ingredient (5) are dissolved in an ingredient (6), and then an ingredient (1) and, if necessary, auxiliaries such as a dispersing agent (preferably polyvinyl alcohol) and a defoamer are added. After mixing, the mixture is emulsified by a homomixer or the like to obtain an emulsion. Separately, an ingredient (3) and/or an ingredient (4), and/or an ingredient (5) are dissolved in an ingredient (6) and then an ingredient (2) and, if necessary, auxiliaries such as a dispersing agent and a defoamer are added. After mixing, the mixture is subjected to pulverization/suspension by a wet milling technique using media such as glass beads and zirconia beads to obtain a suspension. The emulsion is mixed with the suspension and, if necessary, auxiliaries such as a defoamer, a thickener, a preservative agent and an antifreezing agent are added.

Method 3: An ingredient (3), an ingredient (4), and an ingredient (5) are dissolved in an ingredient (6), and then an ingredient (1) and, if necessary, auxiliaries such as a dispersing agent and a defoamer are added. After mixing, the mixture is emulsified by a homomixer or the like to obtain an emulsion. To the emulsion, an ingredient (2) is added and, if necessary, auxiliaries such as a dispersing agent and a defoamer are added. After mixing, the mixture is subjected to pulverization/suspension by a wet milling technique using media such as glass beads and zirconia beads and, if necessary, auxiliaries such as a defoamer, a thickener, a preservative agent and an antifreezing agent are added.

Method 4: An ingredient (3), an ingredient (4), and an ingredient (5) are dissolved in an ingredient (6), and then an ingredient (2) and, if necessary, auxiliaries such as a dispersing agent and a defoamer are added. After mixing, the mixture is subjected to pulverization/suspension by a wet milling technique using media such as glass beads and zirconia beads to obtain a suspension. To the suspension, an ingredient (1) is added and, if necessary, auxiliaries such as a dispersing agent (preferably polyvinyl alcohol) and a defoamer are added. After mixing, the mixture is emulsified by a homomixer or the like and, if necessary, auxiliaries such as a defoamer, a thickener, a preservative agent, antifreezing agent are added.

EXAMPLES

The present invention will be described in more detail below by way of Production Examples and Test Examples, but the present invention is not limited to these Examples.

First, Production Examples are shown. Trade names disclosed in Production Examples are as follows.

Solvesso 150: Aromatic hydrocarbon solvent (mainly containing C10-11 alkylbenzene) [manufactured by ExxonMobil Chemical Company]

Solvesso 200ND: Aromatic hydrocarbon solvent (mainly containing alkyl naphthalene having 11 to 14 carbon atoms in total) [manufactured by ExxonMobil Chemical Company]

Exxsol D110: Mixed solvent of paraffin and cycloparaffin [manufactured by ExxonMobil Chemical Company]

Soprophor FLK: Polyoxyethylene tristyryl phenyl ether phosphoric acid potassium salt [manufactured by Rhodia, Inc.]

REAX 910: Sodium ligninsulfonate [manufactured by MeadWestvaco Corporation]

STEP-FLOW 26: Polyoxyethylene-polyoxypropylene block copolymer [manufactured by Stepan Company]

PVA-205: Polyvinyl alcohol [manufactured by Kuraray Co., Ltd.]

Antifoam C Emulsion: Silicone-based defoamer [manufactured by Dow Corning Corporation]

Kelzan S: Xanthan gum [manufactured by Kelco Corp.]

VEEGUM Granules: Aluminum magnesium silicate [manufactured by Vanderbilt Corp.]

Proxel GXL: Preservative agent [manufactured by Avecia, Inc.]

DYNO-MILL: Beads mill [manufactured by Shinmaru Enterprises Corporation]

T.K. autohomomixer: Homogenizer [manufactured by Tokushu Kika Kogyo Co., Ltd.]

Mastersizer 2000: Laser diffraction particle size distribution analyzer [manufactured by Sysmex Corporation]

Production Example 1

Esfenvalerate (purity: 86.5%) (91.84 g) was mixed with 158.88 g of Solvesso 150 to obtain a homogeneous solution, thus preparing. an oil phase. To 297.90 g of deionized water, 0.99 g of Antifoam C Emulsion, 7.94 g of Soprophor FLK, 9.93 g of STEP-FLOW 26, and 25.82 g of REAX 910 were added, followed by mixing with stirring to prepare an aqueous phase. To the aqueous phase, 50.00 g of clothianidin (purity: 99.3%) was added, followed by mixing with stirring. Furthermore, the oil phase thus prepared (250.72 g) was added thereto, followed by mixing with stirring. The obtained mixture was wet-milled using a DYNO-MILL (1.0 mm glass beads, filling rate of 80%, circumferential velocity of 10 m/s) to obtain a suspoemulsion A.

Kelzan S (1.49 g), 2.98 g of VEEGUM Granules, 1.99 g of Proxel GXL, 44.69 g of propylene glycol, 0.99 g of Antifoam C Emulsion, and 327.35 g of deionized water were mixed to prepare a thickener solution. The thickener solution was mixed with the suspoemulsion A to obtain a suspoemulsion of the present invention, which contains 5 w/v % of clothianidin and 8 w/v % of esfenvalerate.

The solubility of clothianidin in 100 g of the oil phase composed of esfenvalerate and Solvesso 150 at 25° C. was 0.003 g.

Production Example 2

To 49.65 g of deionized water, 0.50 g of Antifoam C Emulsion, 7.94 g of Soprophor FLK, and 12.91 g of REAX 910 were added, followed by mixing with stirring to prepare an aqueous phase. To the mixture, 50.00 g of clothianidin (purity: 99.3%) was added, followed by mixing with stirring. The mixture thus obtained was wet-milled using a DYNO-MILL (1.0 mm glass beads, filling rate of 80%, circumferential velocity of 10 m/s) to obtain a clothianidin suspension.

Meanwhile, 91.84 g of esfenvalerate (purity: 86.5%) was mixed with 158.88 g of Solvesso 150 to obtain a homogeneous solution, thus preparing an oil phase. To 248.25 g of deionized water, 0.50 g of Antifoam C Emulsion, 9.93 g of STEP-FLOW 26, and 12.91 g of REAX 910 were added, followed by mixing with stirring to prepare an aqueous phase. The oil phase was mixed with the aqueous phase. The mixture thus obtained was stirred using a T.K. autohomomixer to obtain an esfenvalerate emulsion.

Kelzan S (1.49 g), 2.98 g of VEEGUM Granules, 1.99 g of Proxel GXL, 44.69 g of propylene glycol, 0.99 g of Antifoam C Emulsion, and 327.35 g of deionized water were mixed to prepare a thickener solution. The thickener solution, the suspension and the emulsion were mixed to obtain a suspoemulsion of the present invention, which contains 5 w/v % of clothianidin and 8 w/v % of esfenvalerate.

The solubility of clothianidin in 100 g of the oil phase composed of esfenvalerate and Solvesso 150 at 25° C. was 0.003 g.

Production Example 3

To 49.65 g of deionized water, 0.50 g of Antifoam C Emulsion, 7.94 g of Soprophor FLK, and 6.45 g of REAX 910 were added, followed by mixing with stirring to prepare an aqueous phase. To the aqueous phase, 50.00 g of clothianidin (purity: 99.3%) was added, followed by mixing with stirring. The mixture thus obtained was wet-milled using a DYNO-MILL (1.0 mm glass beads, filling rate of 80%, circumferential velocity of 10 m/s) to obtain a clothianidin suspension.

Meanwhile, 91.84 g of esfenvalerate (purity: 86.5%) was mixed with 158.88 g of Solvesso 150 to obtain a homogeneous solution, thus preparing an oil phase. To 355.00 g of deionized water, 1.49 g of Antifoam C Emulsion, 19.86 g of STEP-FLOW 26, and 49.65 g of PVA-205 was added, followed by mixing with stirring to prepare an aqueous phase. The oil phase was mixed with the aqueous phase. The mixture thus obtained was stirred using a T.K. autohomomixer to obtain an esfenvalerate emulsion.

Kelzan S (1.49 g), 2.98 g of VEEGUM Granules, 1.99 g of Proxel GXL, 44.69 g of propylene glycol, and 170.46 g of deionized water were mixed to prepare a thickener solution. The thickener solution, the suspension and the emulsion were mixed to obtain a suspoemulsion of the present invention, which contains 5 w/v % of clothianidin and 8 w/v % of esfenvalerate.

The solubility of clothianidin in 100 g of the oil phase composed of esfenvalerate and Solvesso 150 at 25° C. was 0.003 g.

Production Example 4

Esfenvalerate (purity: 86.5%) (91.84 g) was mixed with 158.88 g of Solvesso 150 to obtain a homogeneous solution, thus preparing an oil phase. To 297.90 g of deionized water, 0.99 g of Antifoam C Emulsion, 7.94 g of Soprophor FLK, 9.93 g of STEP-FLOW 26, and 25.82 g of REAX 910 were added, followed by mixing with stirring to prepare an aqueous phase. To this aqueous phase, 50.00 g of clothianidin (purity: 99.3%) was added, followed by mixing with stirring. Furthermore, 250.72 g of the oil phase thus prepared was added thereto, followed by mixing with stirring. The mixture thus obtained was wet-milled using a DYNO-MILL (1.0 mm glass beads, filling rate of 801, circumferential velocity of 10 m/s) to obtain a suspoemulsion B.

Kelzan S (2.18 g), 4.37 g of VEEGUM Granules, 1.99 g of Proxel GXL, 44.69 g of propylene glycol, 0.99 g of Antifoam C Emulsion, and 315.34 g of deionized water were mixed to prepare a thickener solution. The thickener solution was mixed with the suspoemulsion B to obtain a suspoemulsion of the present invention, which contains 5 w/v % of clothianidin and 8 w/v % of esfenvalerate.

The solubility of clothianidin in 100 g of the oil phase composed of esfenvalerate and Solvesso 150 at 25° C. was 0.003 g.

Production Example 5

Esfenvalerate (purity: 86.5%) (91.84 g) was mixed with 158.88 g of Solvesso 150 to obtain a homogeneous solution, thus preparing an oil phase. To 297.90 g of 300 ppm hard water, 0.99 g of Antifoam C Emulsion, 7.94 g of Soprophor FLK, 9.93 g of STEP-FLOW 26, and 25.82 g of REAX 910 were added, followed by mixing with stirring to prepare an aqueous phase. To the aqueous phase, 50.00 g of clothianidin (purity: 99.3%) was added, followed by mixing with stirring. Furthermore, 250.72 g of the oil phase thus prepared was added thereto, followed by mixing with stirring. The mixture thus obtained was wet-milled using a DYNO-MILL (1.0 mm glass beads, filling rate of 80%, circumferential velocity of 10 m/s) to obtain a suspoemulsion C.

Kelzan S (2.18 g), 4.37 g of VEEGUM Granules, 1.99 g of Proxel GXL, 44.69 g of propylene glycol, 0.99 g of Antifoam C Emulsion, and 315.34 g of 300 ppm hard water were mixed to prepare a thickener solution. The thickener solution was mixed with the suspoemulsion C to obtain a suspoemulsion of the present invention, which contains 5 w/v % of clothianidin and 8 w/v % of esfenvalerate.

The solubility of clothianidin in 100 g of the oil phase composed of esfenvalerate and Solvesso 150 at 25° C. was 0.003 g.

Production Example 6

Esfenvalerate (purity: 86.5%) (34.44 g) was mixed with 89.37 g of Solvesso 200ND to obtain a homogeneous solution, thus preparing an oil phase. To 317.76 g of deionized water, 0.99 g of Antifoam C Emulsion, 7.94 g of Soprophor FLK, 2.48 g of STEP-FLOW 26, and 25.82 g of REAX 910 were added, followed by mixing with stirring to prepare an aqueous phase. To this aqueous phase, 200.00 g of clothianidin (purity: 99.3%) was added, followed by mixing with stirring. Furthermore, 123.81 g of the oil phase thus prepared was added thereto, followed by mixing with stirring. The mixture thus obtained was wet-milled using a DYNO-MILL (1.0 mm glass beads, filling rate of 80%, circumferential velocity of 10 m/s) to obtain a suspoemulsion D.

Kelzan S (1.49 g), 2.98 g of VEEGUM Granules, 1.99 g of Proxel GXL, 44.69 g of propylene glycol, 0.99 g of Antifoam C Emulsion, and 351.43 g of deionized water were mixed to prepare a thickener solution. The thickener solution was mixed with the suspoemulsion D to obtain a suspoemulsion of the present invention, which contains 20 w/v % of clothianidin and 3 w/v % of esfenvalerate.

Production Example 7

Tolclofos-methyl (purity: 96.9%) (51.24 g) was mixed with 198.60 g of Solvesso 150 to obtain a homogeneous solution, thus preparing an oil phase. To 297.90 g of deionized water, 4.37 g of VEEGUM Granules, 1.99 g of Antifoam C Emulsion, 7.94 g of Soprophor FLK, 9.93 g of STEP-FLOW 26, and 25.82 g of REAX 910 were added, followed by mixing with stirring to prepare an aqueous phase. To this aqueous phase, 50.00 g of clothianidin (purity: 99.3%) was added, followed by mixing with stirring. Furthermore, 249.84 g of the oil phase thus prepared was added thereto, followed by mixing with stirring. The mixture thus obtained was wet-milled using a DYNO-MILL (1.0 mm glass beads, filling rate of 801, circumferential velocity of 10 m/s) to obtain a suspoemulsion E.

Kelzan S (2.18 g), 1.99 g of Proxel GXL, 44.69 g of propylene glycol, and 327.04 g of deionized water were mixed to prepare a thickener solution. The thickener solution was mixed with the suspoemulsion E to obtain a suspoemulsion of the present invention, which contains 5 w/v % of clothianidin and 5 w/v % of tolclofos-methyl.

The solubility of clothianidin in 100 g of the oil phase composed of tolclofos-methyl and Solvesso 150 at 25° C. was 0.002 g.

Production Example 8

Pyridalyl (purity: 94.5%) (65.67 g) was mixed with 85.77 g of Exxaol D110 to obtain a homogeneous solution, thus preparing an oil phase. To 297.90 g of deionized water, 4.37 g of VEEGUM Granules, 3.97 g of Antifoam C Emulsion, 23.83 g of Soprophor FLK, 9.93 g of STEP-FLOW 26, and 25.82 g of REAX 910 were added, followed by mixing with stirring to prepare an aqueous phase. To this aqueous phase, 50.00 g of clothianidin (purity: 99.3%) was added, followed by mixing with stirring. Furthermore, 151.45 g of the oil phase thus prepared was added thereto, followed by mixing with stirring. The mixture thus obtained was wet-milled using a DYNO-MILL (1.0 mm glass beads, filling rate of 80%, circumferential velocity of 10 m/s) to obtain a suspoemulsion F.

Kelzan S (2.18 g), 1.99 g of Proxel GXL, 44.69 g of propylene glycol, and 398.62 g of deionized water were mixed to prepare a thickener solution. The thickener solution was mixed with the suspoemulsion F to obtain a suspoemulsion of the present invention, which contains 5 w/v % of clothianidin and 6.25 w/v % of pyridalyl.

The solubility of clothianidin in 100 g of the oil phase composed of pyridalyl and Exxsol D110 at 25° C. was 0.009 g.

Production Example 9

Pyridalyl (purity: 94.5%) (65.21 g) was mixed with 85.17 g of Exxsol D110 to obtain a homogeneous solution, thus preparing an oil phase. To 295.80 g of deionized water, 4.34 g of VEEGUM Granules, 3.94 g of Antifoam C Emulsion, 23.66 g of Soprophor FLK, 9.86 g of STEP-FLOW 26, and 25.64 g of REAX 910 were added, followed by mixing with stirring to prepare an aqueous phase. To this aqueous phase, 50.00 g of fthalide (purity: 98.6%) was added, followed by mixing with stirring. Furthermore, 150.38 g of the oil phase thus prepared was added thereto, followed by mixing with stirring. The mixture thus obtained was wet-milled using a DYNO-MILL (1.0 mm glass beads, filling rate of 80%, circumferential velocity of 10 m/s) to obtain a suspoemulsion G.

Kelzan S (2.17 g), 1.97 g of Proxel GXL, 44.37 g of propylene glycol, and 398.32 g of deionized water were mixed to prepare a thickener solution. The thickener solution was mixed with the suspoemulsion a to obtain a suspoemulsion of the present invention, which contains 5 w/v % of fthalide and 6.25 w/v % of pyridalyl.

Production Example 10

Pyridalyl (purity: 94.5%) (65.87 g) was mixed with 86.03 g of Exxsol D110 to obtain a homogeneous solution thus preparing an oil phase. To 298.80 g of deionized water, 4.38 g of VEEGUM Granules, 3.98 g of Antifoam C Emulsion, 23.90 g of Soprophor FLK, 9.96 g of STEP-FLOW 26, and 25.90 g of REAX 910 were added, followed by mixing with stirring to prepare an aqueous phase. To this aqueous phase, 50.00 g of furametpyr (purity: 99.6%) was added, followed by mixing with stirring. Furthermore, 151.91 g of the oil phase thus prepared was added, followed by mixing with stirring. The mixture thus obtained was wet-milled using a DYNO-MILL (1.0 mm glass beads, filling rate of 80%, circumferential velocity of 10 m/s) to obtain a suspoemulsion H.

Kelzan S (2.19 g), 1.99 g of Proxel GXL, 44.82 g of propylene glycol, and 392.51 g of deionized water were mixed to prepare a thickener solution. The thickener solution was mixed with the suspoemulsion H to obtain a suspoemulsion of the present invention, which contains 5 w/v % of furametpyr and 6.25 w/v % of pyridalyl.

The solubility of furametpyr in 100 g of the oil phase composed of pyridalyl and Exxsol D110 at 25° C. was 0.394 g.

Production Example 11

Pyridalyl (purity: 94.5%) (64.95 g) was mixed with 84.82 g of Exxsol D110 to obtain a homogeneous solution, thus preparing an oil phase. To 294.60 g of deionized water, 4.32 g of VEEGUM Granules, 3.93 g of Antifoam C Emulsion, 23.57 g of Soprophor FLK, 9.82 g of STEP-FLOW 26, and 25.53 g of REAX 910 were added, followed by mixing with stirring to prepare an aqueous phase. To this aqueous phase, 50.00 g of isotianil (purity: 98.2%) was added, followed by mixing with stirring. Furthermore, 149.77 g of the oil phase thus prepared was added thereto, followed by mixing with stirring. The mixture thus obtained was wet-milled using a DYNO-MILL (1.0 mm glass beads, filling rate of 80%, circumferential velocity of 10 m/s) to obtain a suspoemulsion I.

Kelzan S (2.16 g), 1.96 g of Proxel GXL, 44.19 g of propylene glycol, and 379.81 g of deionized water were mixed to prepare a thickener solution. The thickener solution was mixed with the suspoemulsion I to obtain a suspoemulsion of the present invention, which contains 5 w/v % of isotianil and 6.25 w/v % of pyridalyl.

The solubility of isotianil in 100 g of the oil phase composed of pyridalyl and Exxsol D110 at 25° C. was 0.020 g.

Production Example 12

Pyridalyl (purity: 94.5%) (64.48 g) was mixed with 84.22 g of Exxsol D110 to obtain a homogeneous solution, thus preparing an oil phase. To 292.50 g of deionized water, 4.29 g of VEEGUM Granules, 3.90 g of Antifoam C Emulsion, 23.40 g of Soprophor FLK, 9.75 g of STEP-FLOW 26, and 25.35 g of REAX 910 were added, followed by mixing with stirring to prepare an aqueous phase. To the aqueous phase, 50.00 g of ferimzone (purity: 97.5%) was added, followed by mixing with stirring. Furthermore, 148.70 g of the oil phase thus prepared was added thereto, followed by mixing with stirring. The mixture thus obtained was wet-milled using a DYNO-MILL (1.0 mm glass beads, filling rate of 80%, circumferential velocity of 10 m/s) to obtain a suspoemulsion J.

Kelzan S (2.15 g), 1.95 g of Proxel GXL, 43.88 g of propylene glycol, and 379.67 g of deionized water were mixed to prepare a thickener solution. The thickener solution was mixed with the suspoemulsion J to obtain a suspoemulsion of the present invention, which contains 5 w/v % of ferimzone and 6.25 w/v % of pyridalyl.

The solubility of ferimzone in 100 g of the oil phase composed of pyridalyl and Exxsol D110 at 25'C was 0.642 g.

Production Example 13

Pyridalyl (purity: 94.5%) (65.81 g) was mixed with 85.95 g of Exxsol D110 to obtain a homogeneous solution, thus preparing an oil phase. To 298.50 g of deionized water, 4.38 g of VEEGUM Granules, 3.98 g of Antifoam C Emulsion, 23.88 g of Soprophor FLK, 9.95 g of STEP-FLOW 26, and 25.87 g of REAX 910 were added, followed by mixing with stirring to prepare an aqueous phase. To this aqueous phase, 50.00 g of ethaboxam (purity: 99.5%) was added, followed by mixing with stirring. Furthermore, 151.75 g of the oil phase thus prepared was added thereto, followed by mixing with stirring. The mixture thus obtained was wet-milled using a DYNO-MILL (1.0 mm glass beads, filling rate of 80%, circumferential velocity of 10 m/s) to obtain a suspoemulsion K.

Kelzan S (2.19 g), 1.99 g of Proxel GXL, 44.78 g of propylene glycol, and 391.47 g of deionized water were mixed to prepare a thickener solution. The thickener solution was mixed with the suspoemulsion K to obtain a suspoemulsion of the present invention, which contains 5 w/v % of ethaboxam and 6.25 w/v % of pyridalyl.

The solubility of ethaboxam in 100 g of the oil phase composed of pyridalyl and Exxsol D110 at 25° C. was 0.003 g.

Test Example 1

The volume median diameter of the suspoemulsions obtained in Production Examples 1 to 13 was measured by Mastersizer 2000, immediately after production or after storage under prescribed conditions. The results are shown in Table 1.

TABLE 1

| | Immediately after production | After storage at 54° C. for 2 weeks | After storage at −20° C. for 1 month |
|---|---|---|---|
| Production Example 1 | 1.4 μm | 1.4 μm | 1.4 μm |
| Production Example 2 | 1.2 μm | 1.2 μm | 1.2 μm |
| Production Example 3 | 1.6 μm | 1.5 μm | 1.6 μm |
| Production Example 4 | 1.3 μm | 1.4 μm | 1.3 μm |
| Production Example 5 | 1.2 μm | 1.5 μm | 1.3 μm |
| Production Example 6 | 1.3 μm | 1.5 μm | 1.2 μm |
| Production Example 7 | 2.8 μm | 2.5 μm | 3.0 μm |
| Production Example 8 | 1.4 μm | 1.5 μm | 1.4 μm |
| Production Example 9 | 1.8 μm | 1.9 μm | 1.8 μm |
| Production Example 10 | 1.5 μm | 1.6 μm | 1.5 μm |
| Production Example 11 | 2.6 μm | 2.1 μm | 2.5 μm |
| Production Example 12 | 1.5 μm | 1.6 μm | 1.5 μm |
| Production Example 13 | 1.6 μm | 1.7 μm | 1.6 μm |

Test Example 2

The suspoemulsions obtained in Production Examples 1 to 13 were visually observed whether or not an aggregate exists immediately after production, and also visually observed whether or not a change in appearance and formation of a hard cake occur after storage under prescribed conditions. The results are shown in Table 2.

TABLE 2

| | Immediately after production Aggregate | After storage at 54° C. for 2 weeks | | After storage at −20° C. for 1 month | |
|---|---|---|---|---|---|
| | | Appearance | Hard cake | Appearance | Hard cake |
| Production Example 1 | None | No change | None | No change | None |
| Production Example 2 | None | No change | None | No change | None |
| Production Example 3 | None | No change | None | No change | None |
| Production Example 4 | None | No change | None | No change | None |
| Production Example 5 | None | No change | None | No change | None |
| Production Example 6 | None | No change | None | No change | None |
| Production Example 7 | None | No change | None | No change | None |
| Production Example 8 | None | No change | None | No change | None |
| Production Example 9 | None | No change | None | No change | None |
| Production Example 10 | None | No change | None | No change | None |
| Production Example 11 | None | No change | None | No change | None |
| Production Example 12 | None | No change | None | No change | None |
| Production Example 13 | None | No change | None | No change | None |

Test Example 3

The separation rate of the suspoemulsions obtained in Production Examples 1 to 13 was measured after storage at 54° C. for 2 weeks. The separation rate of the suspoemulsion was indicated by a ratio (%) of the height of the supernatant portion (aqueous phase) to the height (5 cm) of the entire liquid. The results are shown in Table 3.

TABLE 3

| | Separation rate (%) after storage at 54° C. for 2 weeks |
|---|---|
| Production Example 1 | 3 |
| Production Example 2 | 0 |
| Production Example 3 | 4 |
| Production Example 4 | 2 |
| Production Example 5 | 1 |
| Production Example 6 | 4 |
| Production Example 7 | <1 |
| Production Example 8 | <1 |
| Production Example 9 | <1 |
| Production Example 10 | <1 |
| Production Example 11 | <1 |
| Production Example 12 | <1 |
| Production Example 13 | <1 |

INDUSTRIAL APPLICABILITY

The suspoemulsion of the present invention is a formulation having excellent storage stability, which suppresses the particle growth of dispersoids of an ingredient (1) and an ingredient (2) during storage at high temperature and low temperature, and causes neither aggregation nor separation of dispersoids, nor formation of a hard cake, nor a change in appearance.

The invention claimed is:

1. A suspoemulsion comprising the following ingredients (1), (2), (3), (4), (5), and (6):
    an ingredient (1): low water-soluble liquid pesticidal ingredient,
    an ingredient (2): low water-soluble pesticidal active ingredient which is solid at normal temperature,
    an ingredient (3): polyoxyalkylene block copolymer,
    an ingredient (4): phosphate ester salt and/or sulfate ester salt of polyoxyethylene aryl phenyl ether,
    an ingredient (5): ligninsulfonic acid salt, and
    an ingredient (6): water.

2. The suspoemulsion according to claim 1, wherein the respective amounts of the ingredients (1), (2), (3), (4), (5), and (6) are 0.1 to 49.5 w/v %, 0.1 to 49.5 w/v %, 0.1 to 10 w/v %, 0.1 to 10 w/v %, 0.1 to 10 w/v %, and 50 to 99.5 w/v %, based on the total amount.

3. The suspoemulsion according to claim 1, wherein the ingredient (1) is a low water-soluble pesticidal active ingredient which is liquid at normal temperature.

4. The suspoemulsion according to claim 1, wherein the ingredient (1) is in a state that a low water-soluble pesticidal active ingredient is dissolved in a hydrophobic liquid.

5. The suspoemulsion according to claim 3, wherein the low water-soluble pesticidal active ingredient is an insecticidal active ingredient.

6. The suspoemulsion according to claim 3, wherein the low water-soluble pesticidal active ingredient is a pyrethroid compound.

7. The suspoemulsion according to claim 3, wherein the low water-soluble pesticidal active ingredient is esfenvalerate.

8. The suspoemulsion according to claim 1, wherein the ingredient (2) is an insecticidal active ingredient.

9. The suspoemulsion according to claim 1, wherein the ingredient (2) is a neonicotinoid compound.

10. The suspoemulsion according to claim 1, wherein the ingredient (2) is clothianidin.

11. The suspoemulsion according to claim 2, wherein the ingredient (1) is a low water-soluble pesticidal active ingredient which is liquid at normal temperature.

12. The suspoemulsion according to claim 2, wherein the ingredient (1) is in a state that a low water-soluble pesticidal active ingredient is dissolved in a hydrophobic liquid.

13. The suspoemulsion according to claim 4, wherein the low water-soluble pesticidal active ingredient is an insecticidal active ingredient.

14. The suspoemulsion according to claim 4, wherein the low water-soluble pesticidal active ingredient is a pyrethroid compound.

15. The suspoemulsion according to claim 4, wherein the low water-soluble pesticidal active ingredient is esfenvalerate.

* * * * *